United States Patent
Tomasi et al.

(10) Patent No.: US 10,519,104 B2
(45) Date of Patent: Dec. 31, 2019

(54) SAFE AND EFFICIENT PROCESS FOR THE PREPARATION OF CARMUSTINE

(71) Applicant: NerPharMa S.r.l., Nerviano (Milan) (IT)

(72) Inventors: Attilio Tomasi, Milan (IT); Ilaria Candiani, Busto Arsizio (IT); Francesco Corcella, Busto Garolfo (IT); Francesco Saverio Caldarelli, Milan (IT)

(73) Assignee: NerPharMa S.r.l., Nerviano (Milan) (IT)

( * ) Notice: Subject to any disclaimer, the term of this patent is extended or adjusted under 35 U.S.C. 154(b) by 0 days.

(21) Appl. No.: 15/444,776

(22) Filed: Feb. 28, 2017

(65) Prior Publication Data

US 2017/0253557 A1    Sep. 7, 2017

(30) Foreign Application Priority Data

Mar. 2, 2016   (IT) .................. 102016000021748

(51) Int. Cl.
| | |
|---|---|
| *C07C 273/18* | (2006.01) |
| *C07C 275/08* | (2006.01) |
| *C07C 275/68* | (2006.01) |
| *C07D 233/60* | (2006.01) |

(52) U.S. Cl.
CPC .. *C07C 273/1854* (2013.01); *C07C 273/1809* (2013.01); *C07C 273/1836* (2013.01); *C07C 275/08* (2013.01); *C07C 275/68* (2013.01); *C07D 233/60* (2013.01)

(58) Field of Classification Search
None
See application file for complete search history.

(56) References Cited

U.S. PATENT DOCUMENTS

| | | | |
|---|---|---|---|
| 4,028,410 A | 6/1977 | Yanko et al. | |
| 6,096,923 A * | 8/2000 | McWilliams | ..... C07C 273/1854 564/33 |

OTHER PUBLICATIONS

Padiya ("Unprecedented 'In Water' Imidazole Carbonylation: Paradigm Shift for Preparation of Urea and Carbamate" Org. Lett., 14, 2012, pp. 2814-2817) (Year: 2012).*
Johnston ("The Synthesis of Antineoplastic Agents. XXXII. N-Nitrosoureas. I." J. Med. Chem., 6, 1963, pp. 669-681) (Year: 1963).*
Casey ("Ch. 9: Working Up the Reaction" Advanced Practical Organic Chemistry, 1990, pp. 141-187) (Year: 1990).*
Sigma Aldrich ("Adsorbents for use as Purification Media" downloaded from https://web.archive.org/web/20140420084244/http://www.sigmaaldrich.com/analytical-chromatography/purification/inorganic-adsorbents.html, captured by the wayback machine on May 20, 2014, pp. 1-2) (Year: 2014).*
Evans pKa Table (downloaded from http://evans.rc.fas.harvard.edu/pdf/evans_pKa_table.pdf on May 8, 2018).*
Averill, "16.2 A Qualitative Description of Acid-Base Equilibriums", General Chemistry: Principles, Patterns, and Applications, published in 2011, downloaded from https://saylordotorg.github.io/text_general-chemistry-principles-patterns-and-applications-v1.0/s20-02-a-qualitative-description-of-a.html on May 9, 2018.*
Carmustine (Merck Index, downloaded from https://www.rsc.org/Merck-Index/monograph/m3115/carmustine?q=authorize on May 9, 2018).*
Gress ("Thio-Click Modification of Poly[2-(3-butenyl)-2-oxazoline" Macromolecules 2007, 40, pp. 7928-7933) (Year: 2007).*
Issad ("Synthesis of Water-Soluble Large Naturalised Dyes" Eur. J. Org. Chem. 2009, 2748-2764) (Year: 2009).*
Search Report and Written Opinion completed in IT UB20161230 on Jun. 8, 2016.
Y. Fuchi et al., "Molecules", vol. 20, pp. 1078-1087 (2015).
J. Lown et al., "J. Org. Chem", vol. 46, pp. 5309-5321 (1981).
K.M. Thelen et al., "Neuroscience Letters", vol. 403, pp. 15-19 (2006).
Partial European Search Report in Application No. EP 17158359, dated Jul. 2017.

* cited by examiner

*Primary Examiner* — Amy C Bonaparte
(74) *Attorney, Agent, or Firm* — Oblon, McClelland, Maier & Neustadt, L.L.P.

(57) ABSTRACT

Carmustine may be safely and efficiently produced by reacting 2-chloroethylamine hydrochloride and 1,1'-carbonyldiimidazole to afford 1,3-bis(2-chloroethyl)-1-urea, followed by nitrosation to give the final product.

12 Claims, No Drawings

SAFE AND EFFICIENT PROCESS FOR THE PREPARATION OF CARMUSTINE

CROSS REFERENCES TO RELATED APPLICATIONS

This application claims priority to Italian Patent Application No. 102016000021748, filed on Mar. 2, 2016, which is incorporated herein by reference in its entirety.

BACKGROUND OF THE INVENTION

Field of the Invention

The present invention relates to processes for the preparation of carmustine. The present invention also relates to intermediate compounds which are useful in such a process and the preparation of such intermediate compounds

Discussion of the Background

Carmustine, which is also known as BCNU (1) and which chemical name is 1,3-bis(2-chloroethyl)-1-nitrosourea, is well known and used for its antitumor properties. In particular, it is used in the treatment of several types of brain cancer (including glioma, glioblastoma multiforme, medulloblastoma, and astrocytoma), colon cancer, lung cancer, multiple myeloma and lymphoma (Hodgkin's and non-Hodgkin). Improvements in the process for its preparation are therefore of great utility.

Several methods have been described for the preparation of BCNU (1), differing in the insertion of the nitroso moiety in either the penultimate or the last step. In the latter case, nitrosation is performed on 1,3-bis(2-chloroethyl)-1-urea (BCU, 2), which represents a highly valuable intermediate.

Preparation of BCU (2), which is also commercially available, is possible according to several synthetic approaches, for example by reaction of aziridine and phosgene (see for example, J. Chem. Soc. 1962, 1481-1487; U.S. Pat. No. 2,288,178, both of which are incorporated herein by reference in their entireties); by reaction of 2-chloroethylamine and phosgene or its analogs (see for example, J. Med. Chem. 1963, Vol. 6, 669-681, and J. Org. Chem. 1981, 46, 5309-5321, both of which are incorporated herein by reference in their entireties); and by reaction of 2-chloroethylamine and 2-chloroethylisocyanate (see for example, J. Org. Chem. 1981, 46, 5309-5321, and J. Pharm. Sciences 1989, Vol. 78, 8, 652-659, both of which are incorporated herein by reference in their entireties). All these preparations employ highly toxic and highly moisture sensitive reagents, like phosgene and triphosgene, which need to be handled with care. Therefore, there is a high need for a safer and more convenient preparation process.

Nitrosation of BCU with dinitrogen trioxide ($N_2O_3$) in dichloromethane is disclosed in U.S. Pat. No. 4,028,410, which is incorporated herein by reference in its entirety. Nitrosation of BCU with sodium nitrite in aqueous formic acid is reported for example in J. Med. Chem. 1963, Vol. 6, p. 669-681, and in J. Org. Chem. 1981, 46, 5309-5321, both of which are incorporated herein by reference in their entireties. U.S. Pat. No. 6,096,923, which is incorporated herein by reference in its entirety, discloses the reaction of a urea derivative with a metal nitrite in a two-phase solvent system comprising an aqueous mineral acid and a non-miscible organic solvent.

However, there remains a need for a safe and efficient process for producing carmustine.

SUMMARY OF THE INVENTION

Accordingly, it is one object of the present invention to provide novel methods for the preparation of carmustine (BCNU (1)).

It is another object of the present invention to provide novel methods for the preparation of carmustine (BCNU (1)) which are safe.

It is another object of the present invention to provide novel methods for the preparation of carmustine (BCNU (1)) which are efficient.

These and other objects, which will become apparent during the following detailed description, have been achieved by the inventors' discovery of a new and efficient process for the preparation of BCNU (1), which employs safe and readily available starting materials under mild reaction conditions and allows for recovery of the product in a good yield and a high purity. For these reasons, such new process is also suitable for plant scale production.

1,1'-carbonyldiimidazole (CDI, 4) is reported to react with amines in water in Org. Lett. 2012, Vol. 14, No. 11, 2814-2817, which is incorporated herein by reference in its entirety, to afford the corresponding N-substituted-carbonylimidazolide. Molecules 2015, 20, 1078-1087, which is incorporated herein by reference in its entirety, discloses the preparation of N-(2-chloroethyl)-1H-imidazole-1-carboxamide (3) upon reaction of 2-chloroethylamine with CDI in acetonitrile in the presence of triethylamine, followed by further reaction without being isolated. CDI has now been found to react with 2-chloroethylamine hydrochloride (5) in aqueous media, optionally in the presence of a base, to afford N-(2-chloroethyl)-1H-imidazole-1-carboxamide (3) which is obtained in good yield and is easily isolated by spontaneous precipitation and subsequent filtration. Such intermediate product can be dried under vacuum and can be stored before being transformed to BCU (2). In fact, it can be reacted with another molecule of 2-chloroethylamine hydrochloride (5) in a solvent, optionally in the presence of a base, resulting in the formation of BCU (2).

Such a two-step procedure can actually be performed even as a one-pot reaction, that is without the need to isolate the intermediate imidazolyl derivative (3). CDI (4) reacts with one equivalent of 2-chloroethylamine hydrochloride (5) in an aqueous medium, optionally in the presence of a base, providing N-(2-chloroethyl)-1H-imidazole-1-carboxamide (3), which precipitates from the reaction mixture. The second reaction occurs with the addition of a second equivalent of 2-chloroethylamine hydrochloride (5) and increasing the reaction temperature. The 1,3-bis(2-chloroethyl)-1-urea (BCU, 2) is easily isolated by filtration and can be used as such for further transformation, i.e. for preparation of BCNU (1).

Improved conditions for BCU (2) nitrosation reaction have then been devised, which involve use of a metal nitrite and formic acid in a specific sequence of steps which allows for an easy reaction progress control. The following work-up procedure gives rise to a highly pure product in very good yield. The metal nitrite, preferably sodium nitrite, is dissolved in an aqueous medium and to such solution BCU (2) and a water-immiscible organic solvent, for example a chlorinated hydrocarbon solvent, are added. BCU (2) is not soluble in these reaction conditions thus a tri-phase mixture, comprising two immiscible solvents and the solid BCU (2), is obtained. To the cooled tri-phase mixture, formic acid is added dropwise thus permitting nitrosation of BCU (2) and dissolution of the reaction product BCNU (1) into the organic phase. When addition of formic acid is finished, the reaction is generally complete, resulting in a two-phase clear solution, from which purification and isolation of BCNU (1) is straightforward.

The whole process is summarized in Scheme 1:

Scheme 1

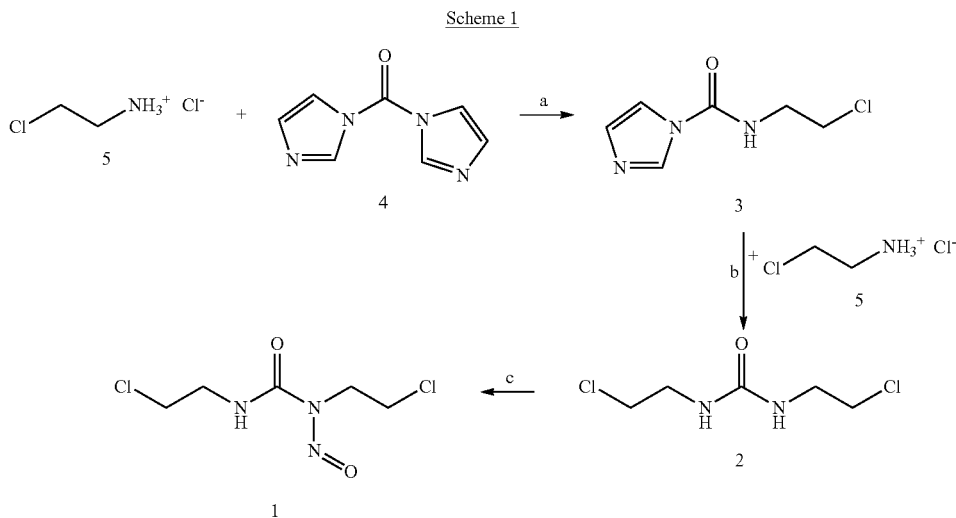

Thus, in a first embodiment, the present invention provides a process for the preparation of 1,3-bis(2-chloroethyl)-1-nitrosourea (BCNU, 1) which comprises:
(a) reacting 2-chloroethylamine hydrochloride (5) with carbonyldiimidazole (CDI, 4) in an aqueous medium;
(b) reacting the resulting imidazolyl derivative N-(2-chloroethyl)-1H-imidazole-1-carboxamide (3)

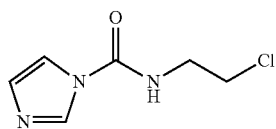

with 2-chloroethylamine hydrochloride (5) in an organic solvent or in an aqueous medium thus obtaining intermediate 1,3-bis(2-chloroethyl)-1-urea (BCU, 2).

In a preferred embodiment, the organic solvent in step (b) is THF.

In another preferred embodiment, step (a) is conducted at a temperature of from 0 to 10° C.

In a further preferred embodiment, the temperature in step (a) is in the range 0 to 5° C., more preferably in the range 0 to 3° C.

Preferably, step (b) is conducted at a temperature of from 20 to 60° C.

Further preferably, the temperature in step (b) is in the range 40 to 45° C., more preferably 40° C.

In a further embodiment, the above process is carried out in the presence of a base, in at least one of steps (a) and (b), independently. As an example, step (a) is carried out in the presence of a base, at a pH in the range 7.5 to 8.5, for instance in the presence of NaOH. In another example, step (b) is carried out in the presence of a base, preferably $K_2CO_3$ or NaOH. In a further example, step (b) is carried out in THF in the presence of $K_2CO_3$ or in an aqueous medium in the presence of NaOH.

Preferably, the process further comprises nitrosation of BCU (2) to give BCNU (1).

In a preferred embodiment, nitrosation of BCU (2) is carried out by performing the following sequence of steps:
(c1) dissolving a metal nitrite in an aqueous medium;
(c2) adding BCU (2) and a water-immiscible organic solvent to the aqueous solution resulting from step (c1) to form a tri-phase reaction mixture;
(c3) adding formic acid to said tri-phase reaction mixture at a temperature in the range 0 to 10° C.; and
optionally isolating BCNU (1) thereby prepared from the organic phase.

Preferably, in step (c1) the metal nitrite is sodium nitrite ($NaNO_2$), in step (c2) the solvent is a chlorinated hydrocarbon solvent, preferably dichloromethane (DCM), and step (c3) is performed at a temperature in the range 0 to 5° C., more preferably 0 to 3° C. Even more preferably, such process further comprises purifying BCNU (1) by filtration of the organic phase through silica gel.

In a second embodiment, the present invention provides a process for the preparation of BCU (2) which comprises:
(a) reacting 2-chloroethylamine hydrochloride (5) with CDI (4) in an aqueous medium;
(b) reacting the resulting imidazolyl derivative N-(2-chloroethyl)-1H-imidazole-1-carboxamide (3) with 2-chloroethylamine hydrochloride (5) in an organic solvent or in an aqueous medium thus obtaining intermediate BCU (2).

In a preferred embodiment, the organic solvent in step (b) is THF.

In another preferred embodiment, step (a) is conducted at a temperature of from 0 to 10° C.

In a further preferred embodiment, the temperature in step (a) is in the range 0 to 5° C., more preferably in the range 0 to 3° C.

Preferably, step (b) is conducted at a temperature of from 20 to 60° C.

Further preferably, the temperature in step (b) is in the range 40 to 45° C., more preferably 40° C.

In a further embodiment, the above process is carried out in the presence of a base, in at least one of steps (a) and (b), independently. As an example, step (a) is carried out in the presence of a base at a pH in the range 7.5 to 8.5, for instance in the presence of NaOH. In another example, step (b) is carried out in the presence of a base, preferably $K_2CO_3$ or NaOH. In a further example, step (b) is carried out in THF in the presence of $K_2CO_3$ or in an aqueous medium in the presence of NaOH.

In a third embodiment, the invention provides a process for the preparation of BCU (2) wherein above steps (a) and (b) are performed as a one-pot reaction in an aqueous medium.

In a fourth embodiment, the present invention provides a process for the preparation of BCNU (1) which comprises nitrosation of BCU (2) by a metal nitrite in a solvent in the presence of an acid, by performing the following sequence of steps:
  (c1) dissolving the metal nitrite in an aqueous medium;
  (c2) adding BCU (2) and a water-immiscible organic solvent to the aqueous solution resulting from step (c1) to form a tri-phase reaction mixture;
  (c3) adding formic acid to said tri-phase reaction mixture at a temperature in the range 0 to 10° C.; and
  optionally isolating BCNU (1) thereby prepared from the organic phase.

Preferably, in step (c1) the metal nitrite is $NaNO_2$, in step (c2) the solvent is a chlorinated hydrocarbon solvent, preferably DCM, and step (c3) is performed at a temperature in the range 0 to 5° C., more preferably 0 to 3° C. Even more preferably, such process further comprises purifying BCNU (1) by filtration of the organic phase through silica gel.

Moreover, in a fifth embodiment, the present invention provides the use of intermediate compound (3) as defined above for the preparation of BCU (2).

Finally, in a sixth embodiment, the present invention provides the use of the intermediate compound (3) as defined above for the preparation of BCNU (1).

DETAILED DESCRIPTION OF THE PREFERRED EMBODIMENTS

A detailed mode of realization of the present invention is defined below.

According to step (a), 2-chloroethylamine hydrochloride (5) in an aqueous solution is reacted with CDI (4), which is added in portions, for a time varying from 10 minutes to 96 hours, to provide N-(2-chloroethyl)-1H-imidazole-1-carboxamide (3). Alternatively, an aqueous base is added before addition of CDI, thus obtaining a solution with a pH in the range 7.5 to 8.5, the base being, for example, sodium carbonate ($Na_2CO_3$), $K_2CO_3$, NaOH, or potassium hydroxide (KOH). If a base is added, preferably the pH is about 8, the base is NaOH, more preferably NaOH 10%.

Typically, this step is conducted at a temperature of from 0 to 10° C. The temperature of reaction is preferably in the range 0 to 5° C. The reaction product precipitates directly from the aqueous solution of the reaction medium and is then filtered and dried before being submitted to step (b).

According to step (b), N-(2-chloroethyl)-1H-imidazole-1-carboxamide (3) is reacted with 2-chloroethylamine hydrochloride (5) in an organic solvent, preferably in THF, or in an aqueous medium. Typically, this step is carried out at a temperature of from 20 to 60° C., preferably at about 40° C., for a time varying from 10 minutes to 96 hours to provide BCU (2). Alternatively, a base is also added to the reaction mixture, for example $Na_2CO_3$, $K_2CO_3$, NaOH, KOH, preferably $K_2CO_3$. The solvent is evaporated under vacuum and the product is then precipitated by the addition of water. The obtained suspension is filtered, washed with water and dried.

When steps (a) and (b) are performed as a one-pot reaction, that is as a through or direct process, intermediate (3) is not isolated. CDI (4) reacts with one equivalent of 2-chloroethylamine hydrochloride (5) in an aqueous medium, optionally in the presence of a base, as defined above in step (a), providing intermediate (3), which precipitates from the reaction mixture. The second reaction occurs with the addition in the same reaction vessel of a second equivalent of 2-chloroethylamine hydrochloride (5) and increasing the reaction temperature, preferably to 40 to 45° C. When the reaction is complete, the suspension is cooled to room temperature (20 to 25° C.) and BCU (2) is easily isolated by filtration and drying and can be used as such for the BCNU (1) preparation.

According to step (c), nitrosation of BCU (2) is obtained by adding formic acid dropwise to a tri-phase suspension of BCU (2) in an aqueous solution of a metal nitrite, preferably $NaNO_2$, in the presence of a water-immiscible organic solvent, for example an ether, preferably methyl tert-butyl ether (MTBE), or a chlorinated hydrocarbon solvent, preferably DCM, or toluene. Typically, this step is conducted at a temperature of from 0 to 10° C., preferably 0 to 5° C., more preferably 0 to 3° C., for a time varying from 10 minutes to 96 hours. The isolation of the final product (1), BCNU, is obtained by separating the organic phase from the aqueous phase and washing it with water. The organic phase is then preferably filtered through a silica gel pad. Preferably silica gel is high-purity grade. More preferably, silica gel is for flash chromatography, with pore size 60 Å, 230-400 mesh.

It has been found that 1,2,3-tris-2-chloroethyl biuret of formula (6):

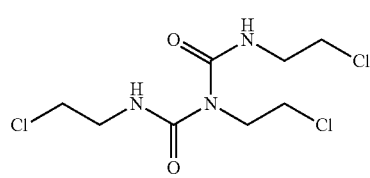

identified by LC-UV-MS, represents a common impurity which is present in the reaction mixture, in particular in the organic phase, at the end of the nitrosation step (c) in an amount range of generally 0.01 to 1 Area % (HPLC). This is the only impurity, let alone unreacted BCU (2), which is detected after the work-up.

The filtration through a silica gel pad permits complete removal of such impurity (6) which becomes undetectable by HPLC in the final product.

The filtered organic BCNU (1) solution is evaporated to residue and the product isolated by crystallisation in organic solvents. As an example, the oily residue is dissolved in a suitable solvent, such as an ether, an aromatic hydrocarbon, an ester or a ketone, preferably MTBE, and is precipitated by the addition of a second solvent, in which BCNU is not soluble, for example a linear or cyclic hydrocarbon, preferably n-heptane. The precipitation is easily obtained by either adding the second solvent dropwise into the BCNU solution or adding the BCNU solution into the second solvent.

In all instances, the aqueous medium may be water. Alternatively, the aqueous medium may contain other components, so long as they do not significantly adversely impact or impede the particular reaction of that step.

Other features of the invention will become apparent in the course of the following descriptions of exemplary embodiments which are given for illustration of the invention and are not intended to be limiting thereof.

EXAMPLES

Analytical Methods

The HPLC method complied with the conditions described for the API (Active Pharmaceutical Ingredient) in the Carmustine monograph USP 37 2014 (United States Pharmacopoeia), using a Zorbax SB C18 (150×4.6 mm; 5 µm) column. Retention times (RT) are given in minutes, the wavelength is 200 nm. Mass are given as m/z ratio.

It was found that this method allows the detection not only of carmustine (BCNU, 1) but also of imidazolyl intermediate (3) and of BCU (2). 2-chloroethylamine hydrochloride (5) cannot be detected by HPLC/UV.

All the HPLC area % data reported herein were generated with the HPLC method in Table 1:

TABLE 1

| HPLC method for API Carmustine (USP 37 2014) HP 1100 Instrument | | |
|---|---|---|
| Column | Zorbax SB C18 150 × 4.6 mm. 5.0 µm | |
| Mobile phase | Acetonitrile/water 30/70 | |
| Flow | 1.5 mL/min. | |
| Column temperature | Room temperature | |
| Autosampler temperature | 5° C. | |
| Wavelength | 200 | |
| Injection volume | 5 µL | |
| Elution Time | 15' | |
| Sample preparation for purity | 1 mg/mL in ACN | |
| Elution time | Intermediate (3) | RT 1.7 |
| | BCU (2) | RT 1.9 |
| | Carmustine (1) | RT 9.3 |
| | 1,2,3-tris-2-chloroethyl biuret (6) | RT 12.4 |

LC-UV-MS data were acquired on a 1100 Series LC/MSD instrument using the ESI(+) ionization technique and a HPLC method that differs from the USP method only for the addition of 0.1% formic acid (HCOOH) to the HPLC eluents.

$^1$H-NMR spectra were recorded in DMSO-$d_6$ at a constant temperature of 28° C. on a Varian INOVA 500 spectrometer operating at 499.55 MHz and equipped with a 5 mm z-axis PFG Indirect Detection Probe ($^1$H{$^{15}$N-$^{31}$P}). Chemical shifts (δ) are reported in parts per million (ppm) and coupling constants (J) in Hz. The following abbreviations are used for multiplicities: s=singlet; d=doublet; t=triplet; q=quartet, m=multiplet; dd=double doublet.

Quantitative $^1$H NMR spectra were recorded according to the method described in Organic Process Research and Development, 2004, Vol. 8, 381-384, which is incorporated herein by reference in its entirety.

The following examples intend to illustrate the invention without limitation as to the scope of the same.

Example 1—Preparation of BCNU (1)

Step a. Preparation of Intermediate N-(2-chloroethyl)-1H-imidazole-1-carboxamide (3)

In a reactor, 1.4 L of water were loaded and cooled to 0 to 3° C. 2-chloroethylamine hydrochloride (5) (200 g, 1.72 mol) was added, and the mixture was stirred to obtain a solution (measured pH is about 6.3). To the stirred solution, CDI (4) (300 g, 1.85 mol) was added portion-wise keeping the temperature below 10° C. At the end of the addition the reaction mixture was left under stirring at 0 to 5° C. for 4 hours. A white solid precipitated, which was filtered and washed twice with 300 ml of water. The wet product was dried at 45° C. under vacuum for about 18 hours, to provide 252 g dry solid of the title compound.

Yield 85%, HPLC purity 100 Area %.

Step b. Preparation of BCU (2) in THF

In a reactor, 660 g (3.80 mol) of N-(2-chloroethyl)-1H-imidazole-1-carboxamide (3) were loaded in 9.3 L of THF. 2-chloroethylamine hydrochloride (520 g, 4.48 mol) was added, and the reaction mixture was heated to 40 to 45° C. under stirring. The reaction was complete within about 6.5 hours.

Work-up: the solvent was evaporated under vacuum until the end of the distillation. 9.3 L of water were added and the suspension was stirred for 1 hour at 5 to 10° C. The suspension was filtered, and the solid washed twice with 1 L of water; the wet product was dried under vacuum at 40° C. until constant weight, providing 573 g of title product.

Yield 81.4%, HPLC purity 100 Area %.

Step c. Nitrosation of BCU (2)

NaNO$_2$ (677 g, 9.8 mol) was dissolved in 3.4 L water. To the solution, BCU (2) (282 g, 1.52 mol) and DCM (7 L) were added. The mixture was stirred and cooled to 0 to 3° C. To the tri-phase mixture, formic acid (0.425 L, 11.26 mol) was added dropwise during about 30 minutes. At the end of the addition two clear liquid phases were obtained. The mixture was stirred for additional 30 minutes, and the organic phase was sampled. The reaction was considered complete when Area % HPLC of starting material was less than 0.5%.

Work-up: the two phases were separated and the organic phase was washed twice with water (3.3 L×2). The solution was evaporated to a volume of 1.1 L and then eluted through silica gel, pre-packed with DCM (700 grams high-purity grade silica gel for flash chromatography, pore size 60 Å, 230-400 mesh ASTM) with final DCM washing. The collected solvent (3.5 L) was evaporated to residue, keeping the internal temperature lower than 10° C. The residue was taken up with pre-cooled MTBE (1.4 L) and the solution was evaporated to residue. The residue was again taken up with pre-cooled MTBE (0.425 L). To this solution, pre-cooled n-heptane (3.5 L) was added, keeping the temperature between 0 and 3° C. (about 30 minutes). At the end of the addition the stirring was continued for 60 minutes at an internal temperature of 0° C. The suspension was filtered, and the solid was washed with pre-cooled n-heptane (0.45 L). The product was dried under vacuum at room temperature until constant weight to provide 283 g BCNU (1).

Yield 87%, HPLC purity 100 Area % (according to USP 37 2014 United States Pharmacopoeia method), NMR title 99.0%.

None of the used solvents (MTBE, DCM, n-heptane) was detected by $^1$H-NMR.

Example 2—Preparation of BCNU (1) in the Presence of Base

Step a. Preparation of Intermediate N-(2-chloroethyl)-1H-imidazole-1-carboxamide (3) in the Presence of Base In a reactor, 750 mL of water were loaded and cooled to 0 to 5° C. 2-chloroethylamine hydrochloride (5) (100 g, 862 mmol) was added, and the mixture was stirred to obtain a solution. The pH was adjusted to 8 with NaOH 10%, keeping the temperature at 0 to 5° C. To the stirred solution, CDI (4) (150 g, 925 mmol) was added portion-wise during 2 hours. At the end of the addition the reaction mixture was left under stirring at 0 to 5° C. overnight. A white solid precipitated, which was filtered and washed twice with 250 ml of water. 132 g of wet product were obtained, which were dried at 45° C. under vacuum for about 18 hours, to provide 110 g of dry solid.

Yield 73.3%, HPLC purity 100 Area %

$^1$H-NMR (500 MHz), δ (ppm, DMSO-d$_6$): 8.77 (t, J=5.9, 1H), 8.24 (dd, J=1.0, 1.5, 1H), 7.67 (dd, J=1.5, 1.5 Hz, 1H), 7.03 (dd, J=1.0, 1.5 Hz, 1H), 3.75 (t, J=5.9 Hz, 2H), 3.57 (q, J=5.9 Hz, 2H)

Step b. Preparation of BCU (2) in THF in the Presence of Base

In a reactor, 94.4 g (545.8 mmol) of N-(2-chloroethyl)-1H-imidazole-1-carboxamide (3) were loaded in 1350 mL THF. The mixture was stirred at room temperature until a complete solution was obtained. 2-chloroethylamine hydrochloride (75 g, 641.4 mmol) was added, followed by K$_2$CO$_3$ (161 g, 1170 mmol). The reaction mixture was heated to 40° C. stirring thoroughly. The reaction was complete within about 4 hours.

Work-up: the solvent was evaporated under vacuum until the end of the distillation. 1350 mL of water were added, and the suspension was stirred for 20 minutes at room temperature. The suspension was filtered, and the solid washed three times with 200 ml of water; the wet product was dried in a tray drier under vacuum at 45° C. for about 18 hours, providing 90.5 g of dry solid.

Yield 87.2%, HPLC purity 100 Area %

$^1$H-NMR (500 MHz), δ (ppm, DMSO-d$_6$): 6.31 (t, J=6.2, 1H), 3.75 (t, J=6.2, 2H), 3.56 (q, J=6.2 Hz, 211)

Step c. Nitrosation of BCU (2)

NaNO$_2$ (144 g, 2.086 mol, 6.1 eq) was dissolved in 720 mL water. To the solution, BCU (2) (60 g, 0.342 mol) and DCM (1800 mL) were added. The mixture was stirred and cooled to 0 to 3° C. To the tri-phase mixture, formic acid (109.8 g, 2.388 mol, 7 eq) was added dropwise during about 30 to 40 minutes. At the end of the addition two clear liquid phases were obtained. The mixture was stirred for additional 30 minutes and the organic phase was sampled. The reaction was considered complete when Area % HPLC of starting material was less than 0.5%.

Work-up: the two phases were separated, and the organic phase was washed twice with water (720 mL×2). The solution was filtered through a short silica gel pad, pre-packed with DCM (4 grams high-purity grade silica gel for flash chromatography, pore size 60 Å, 230-400 mesh ASTM, per gram of BCU (2) used in the reaction). At the end of the filtration the silica gel pad was washed twice with 200 ml of DCM. The collected solvent was evaporated to residue, keeping the internal temperature lower than 10° C. The residue was taken up with MTBE (90 mL). To this solution, n-heptane (750 mL) was added dropwise during 30 to 40 minutes. During the addition the product started to precipitate. At the end of the addition the stirring was continued for 60 minutes at an internal temperature of 0° C. The suspension was filtered and the solid was washed with n-heptane (50 mL). The product was dried under vacuum at room temperature until constant weight (about 3 hours). 55.8 g of dry product as a yellowish powder were obtained.

Yield 80.4%, HPLC purity 99.7 Area %. The residual content of 2-chloroethylamine was determined with the procedure 3 described in USP 37 2014, United states Pharmacopoeia, and was found within the specification.

None of the used solvents (MTBE, DCM, n-heptane) was detected by $^1$H-NMR.

$^1$H-NMR (500 MHz), δ (ppm, DMSO-d$_6$): 8.95 (t, J=5.6, 1H), 4.09 (t, J=6.4, 2H), 3.75 (t, J=6.3 Hz, 2H), 3.62 (m, 4H)

Example 3

Step b. Preparation of BCU (2) in Water in the Presence of Base

In a reactor, N-(2-chloroethyl)-1H-imidazole-1-carboxamide (3) (1.6 g, 9.2 mmol) was loaded in 7.5 mL of water followed by the addition of 2-chloroethylamine hydrochloride (5) (1.06 g, 9.2 mmol). The reaction mixture was heated to 40° C., and the pH was adjusted to 7.6 with NaOH 10%, and the mixture was stirred thoroughly. The reaction was complete within about 4 hours.

Work-up: The mixture was cooled to 20 to 25° C. and the suspension was filtered, washing the solid three times with 10 mL of water. The wet product was dried in a tray drier under vacuum at 45° C. for about 18 hours, providing 1.8 g of dry solid BCU (2). HPLC purity 100 Area %.

Example 4

Steps a/b as a One-Pot Reaction. Preparation of BCU (2) in Water in the Presence of Base In a reactor, 15 mL of water were loaded and cooled to 0 to 5° C. 2-chloroethylamine hydrochloride (2 g, 17.2 mmol) was added, and the mixture was stirred to obtain a solution. The pH was adjusted to about 8 with NaOH 10%, keeping the temperature at 0 to 5° C. To the stirred solution, CDI (3 g, 18.5 mmol) was added portion-wise during 2 hours. At the end of the addition the reaction mixture was left under stirring at 0 to 5° C. overnight. A white solid precipitated. To the mixture a second addition of 2-chloroethylamine hydrochloride (2 g, 17.2 mmol) was done. The pH was adjusted again to about 8 with NaOH 10%, and the mixture was stirred for 4 hours increasing the temperature to 40 to 45° C. The reaction was considered over when the residual intermediate (3) was less than 0.2%. The suspension was cooled to 20 to 25° C. and was filtered; the solid was washed three times with 4 ml of water; the wet product was dried in a tray drier under vacuum at 45° C. for about 18 hours providing 2.13 g of BCU (2).

Yield 57.7%, HPLC purity 100 Area %.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for the preparation of 1,3-bis(2-chloroethyl)-1-urea, which comprises:

(a) reacting 2-chloroethylamine hydrochloride with carbonyldiimidazole in an aqueous medium in the absence of a base, to obtain N-(2-chloroethyl)-1H-imidazole-1-carboxamide of formula 3:

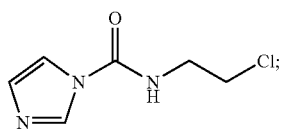

and (b) reacting said N-(2-chloroethyl)-1H-imidazole-1-carboxamide with 2-chloroethylamine hydrochloride in an organic solvent or in an aqueous medium, to obtain 1,3-bis(2-chloroethyl)-1-urea.

2. The process according to claim 1, wherein said organic solvent is THF.

3. The process according to claim 1, wherein said step (a) is conducted at a temperature of from 0 to 10° C. and said step (b) is conducted at a temperature of from 20 to 60° C.

4. The process according to claim 1, wherein said step (a) is conducted at a temperature of from 0 to 5° C. and said step (b) is conducted at a temperature of from 40 to 45° C.

5. The process according to claim 1, wherein said step (b) is carried out in the presence of a base.

6. A process for the preparation of 1,3-bis(2-chloroethyl)-1-nitrosourea, which comprises:

(a) reacting 2-chloroethylamine hydrochloride with carbonyldiimidazole in an aqueous medium in the absence of a base, to obtain N-(2-chloroethyl)-1H-imidazole-1-carboxamide of formula 3:

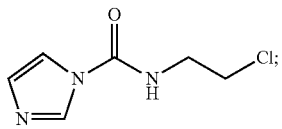

(b) reacting said N-(2-chloroethyl)-1H-imidazole-1-carboxamide with 2-chloroethylamine hydrochloride in an organic solvent or in an aqueous medium, to obtain 1,3-bis(2-chloroethyl)-1-urea; and (c) nitrosation of 1,3-bis(2-chloroethyl)-1-urea to obtain 1,3-bis(2-chloroethyl)-1-nitrosourea.

7. The process according to claim 6, wherein said nitrosation comprises:

(c1) dissolving a metal nitrite in an aqueous medium, to obtain an aqueous solution;

(c2) adding 1,3-bis(2-chloroethyl)-1-urea and a water-immiscible organic solvent to said aqueous solution, to obtain a tri-phase reaction mixture;

(c3) adding formic acid to said tri-phase reaction mixture at a temperature of from 0 to 10° C., to obtain 1,3-bis(2-chloroethyl)-1-nitrosourea; and optionally isolating said 1,3-bis(2-chloroethyl)-1-nitrosourea from the organic phase.

8. The process according to claim 7, wherein:

said metal nitrite is sodium nitrite (NaNO$_2$), said water-immiscible organic solvent is a chlorinated hydrocarbon solvent, and said step (c3) is performed at a temperature of from 0 to 5° C.

9. The process according to claim 7, wherein said water-immiscible organic solvent is dichloromethane.

10. The process according to claim 7, further comprising purifying said 1,3-bis(2-chloroethyl)-1-nitrosourea by filtration of the organic phase through silica gel.

11. The process according to claim 1, wherein said step (a) and said step (b) are performed as a one-pot reaction in an aqueous medium.

12. The process according to claim 6, wherein said organic solvent is THF.

* * * * *